United States Patent [19]

Madden

[11] Patent Number: 5,389,378

[45] Date of Patent: Feb. 14, 1995

[54] BENZOPORPHYRIN VESICLES AND THEIR USE IN PHOTODYNAMIC THERAPY

[75] Inventor: Thomas D. Madden, Vancouver, Canada

[73] Assignee: The Liposome Company, Inc., Princeton, N.J.

[21] Appl. No.: 990,923

[22] Filed: Dec. 15, 1992

Related U.S. Application Data

[63] Continuation of Ser. No. 570,282, Aug. 17, 1990, abandoned.

[51] Int. Cl.⁶ .............................................. A61K 9/127
[52] U.S. Cl. .................................. 424/450; 428/402.2
[58] Field of Search ..... 426/450; 428/402.2; 264/4.1, 4.3, 4.6; 514/410. 908
[58] Field of Search ..... 426/450; 428/402.2; 264/4.1, 4.3, 4.6; 514/410, 908

[56] References Cited

U.S. PATENT DOCUMENTS

| | | | |
|---|---|---|---|
| 4,235,871 | 11/1980 | Papahadjopoulos et al. | 424/19 |
| 4,522,803 | 6/1985 | Lenk et al. | 424/1.1 |
| 4,588,578 | 5/1986 | Fountain et al. | 424/1.1 |
| 4,721,612 | 1/1988 | Janoff et al. | 424/1.1 |
| 4,861,580 | 8/1989 | Janoff et al. | 424/1.1 |
| 4,880,635 | 11/1989 | Janoff et al. | 424/450 |
| 4,913,907 | 4/1990 | Jeri | 424/480 |
| 4,975,282 | 12/1990 | Bally et al. | 424/450 |
| 5,008,050 | 4/1991 | Cullis et al. | 264/4.3 |
| 5,010,073 | 4/1991 | Kappas et al. | 424/450 X |
| 5,053,423 | 10/1991 | Liu | 514/410 |
| 5,077,056 | 12/1991 | Bally et al. | 424/450 |
| 5,091,385 | 2/1992 | Gulliya | 514/224.8 |

FOREIGN PATENT DOCUMENTS 0188329 9/1985 Japan.

OTHER PUBLICATIONS

Mimms Biochemistry, 20, p. 833, 1981.

Allison, et al., "The Plasma Distribution of Benzoporphyrin Derivative and The Effects of Plasma Lipoproteins on its Biodistribution", Photochem Phtobiol, 52, 3, 501–507, 1990.

Cozzani, et al., "Efficient Photosensitization of Malignant Human Cells In Vitro By Liposomes–Bound Porphyrins", Chem. Bio. Interactions, 53, (1985), 131–143.

Goyal, et al., "Photosensitization of Liposomal Membranes by Hematoporphyrin Derivative", Cancer Res, 42,3, 5826–5830, Dec. 1983.

Grossweiner, et al., "Photosensitization of Liposomes by Porphyrins", J. Photochemistry, 25 (1984), 253.

Grossweinger, et al, "Type I and Type II Mechanisms in the Photosensitized Lysis of Phosphatidylcholine Liposomes by Hematoporphyrin", Photochem Photobiol, 36, 159–167, 1982.

Grossweiner, et al., "Photosensitized Lysis of Liposomes by Hematoporphyrin Derivative", Photochem Photobiol, 37, 5, 529–532, 1983.

(List continued on next page.)

*Primary Examiner*—G. S. Kishore
*Attorney, Agent, or Firm*—Joanne Longo Feeney

[57] ABSTRACT

This invention relates to benzoporphyrin containing vesicles which are suitable for pharmaceutical application. In particular, the present invention relates to a liposomal preparation of benzoporphyrin (BPD) incorporated into vesicles comprising a liposome forming lipid such as EPC or DMPC at a drug to lipid ratio of greater than 100 μg/umole lipid which will allow adequate drug dosing with relatively low lipid concentration. In an additional aspect of the present invention, sized liposomes are described which are storage stable. Certain sized BPD-containing vesicles (no greater than about 120 nm in diameter) permit sterilization by terminal filtration. Further, a lyophilized preparation of the BPD-lipid mixture can be obtained from aqueous buffer under conditions which do not result in vesicle fusion/aggregation or BPD precipitation. Liposomes according to the present invention are able to accommodate surprisingly large amounts of BPD within the bilayer of the liposome, rather than in the encapsulated buffer. The advantages of this surprising aspect of the present invention includes the ease of manufacture and the cost savings associated with an efficient use of BPD are also presented.

25 Claims, 3 Drawing Sheets

OTHER PUBLICATIONS

Jamieson, et al., "Preferential Uptake of Banzoporphyrin Derivative By Leukemic Versus Normal Cells", Leukemia Res, 14, 3, 209–219, 1990.

Jori, et al., "Preferential Delivery of Lipsomes–Incorporated Porphyrins to Neoplastic Cells in Tumour–Bearing Rats", Br. J. Cancer, (1983),48,307–309.

Kessel, D., "*In Vitro* Photosensitzation With A Benzoporphyrin Derivative", Photochem Photobiol, 49, 5, 579–582, 1989.

Richter, et al., "Biodistribution of Tritiated Benzoporphyrin Derivative ($^3$H-BPD-MA), A New Potent Photosensitizaer, in Normal and Tumor-Bearing Mice", J. Photoch Photobio, 5 (1990), 231–244.

Richter, et al., "*In vivo* Evaluation of phototoxic Properties of Four Structurally related Banzoporphyrin Derivatives", Photochem Photobiol, 52, 3, 495–500, 1990.

Bagham et al., "Diffusion of Univalent Ions Across the Lamellae of Swollen Phosphaolipids", J. Mol. Bio., 13, 1965, 238–252.

Brault, D., et alk., "Sprectofluorimetric Study of Polyphyrin Incorporation Into Memmbrane Models-evidence for pH effects: Biochiumica et Biophysica Acta", (1986), 857:238–250.

Chen, et al., "Microdetermination of Phosphorus", Anal. Chem., 1956, 28, 1756.

Dinello, et al., "Isolation and Modification of Natural Porphyrins," The Porphyrin, vol. 1, 1978, Academic Press, New York, 290–294.

Doiron, et al., "Photophysics and Dosimetry of Photoradiation Therapy," Porphyrins in Tumor Phototherapy, 281–291, Plenum Press, New York, 1984.

Doughtery,:"In Method in Porphyrin Photosensitization", Kessel, D., ed., 313–328, 1985 Plenum Press, New York.

Doughtery, "Photosensitzation of Helignant Tumors,": Semin. Surg. Oncol., 2:24–37, 1986.

Doughtery, "Studies on the Structure of Porphyrins Contained in Photofrin II", Photochem. Photobiol., 46, 569–575 (1987).

Gomer, "Photohynamic Therapy in the Treatment of Malignancies", Semin. Hematol., 1989, 26(1), 27.

Gruner al., "Novel Multilayered Lipid Vesicles: Comparison of Physical Characteristics of Multilamellar Liposomes and Stable Plurilamellar Vesicles", Biochem., 1985, 24, 2833–2842.

Hope, et al., "Production of Large Unilamallar Vesicles by a Rapid Extrusion Procedure. Characterization of Size Distribution, Trapped Volume and Ability to Maintain a Membrane Potential", Biochemica. Biophysica. Acta, 1985, 812, 55–56.

Kessel, et al., "Chemistry of Hematoporphyrin–Derived Photosensitizers", 46, 563–568, (1987).

McCaughan, "Overview of Experiences with Photodynamic Therapy for Malignancy in 192 Patients", Photochem. Photobiol., 1987, 46, 903–909.

Pangka et al., "Diels–Alder Reactions of Photoporphyrin IX Dimethyl Ester with Electron–Deficient Alkynes", J. Org. Chem., 1986, 51, 1094–1100.

Papahadjopoulos, et al., BBa, 1967, 135, 624–638.

Richter et al., "Preliminary Studies on a More Effectoive Phototoxic Agent than hematoporphyrin", J. Nat. Can. Inst., 1987, 79, 1327.

Zhour, et al., "An Ultrastructual Comparative Evaluation of Tumors Photosensitized by Porphyrins Administered in Aqueous Solution Bound to Liposomes or to Lipoproteins", Photochem. Photobiol., 1988, 48, 487–492.

1

2

R = CO₂CH₃

3

4

BENZOPORPHYRIN VESICLES AND THEIR USE IN PHOTODYNAMIC THERAPY

This is a continuation of copending application Ser. No. 07/570,282 filed on Aug. 17, 1980, now abandoned.

FIELD OF THE INVENTION

This invention relates to benzoporphyrin containing vesicles which are suitable for pharmaceutical application. In particular, the present invention relates to a liposomal preparation of benzoporphyrin (BPD) incorporated into vesicles comprising a liposome forming lipid such as EPC or DMPC at a drug to lipid ratio of greater than about 100 μg/umole lipid which will allow adequate drug dosing with relatively low lipid concentration. In an additional aspect of the present invention, sized liposomes are described which are storage stable. Certain sized BPD-containing vesicles (no greater than about 120 nm in diameter) permit sterilization by terminal filtration. Further, a lyophilized preparation of the BPD-lipid mixture can be obtained from aqueous buffer under conditions which do not result in vesicle fusion/aggregation or BPD precipitation.

Liposomes according to the present invention are able to accommodate surprisingly large amounts of BPD within the bilayer of the liposome, rather than in the encapsulated buffer. The advantages of this surprising aspect of the present invention includes the ease of manufacture and the cost savings associated with an efficient use of BPD are also presented.

In another aspect of the present invention, it has surprisingly been found that liposomes according to the present invention are able to accommodate a significantly greater amount of one analogue of benzoporphyrin, Monoacid A than another analogue, Monoacid B. Liposomes according to the present invention have been made containing Monoacid A in concentrations up to about 209 μg/umole of phospholipid. Liposomes according to the present invention have been made containing Monoacid B in concentrations up to about 55 μg/umole of phospholipid. In liposomes made from mixtures of the Monoacid A and the Monoacid B which contain both Monoacid A and Monoacid B in about a 1:1 weight ratio, the weight ratio of Monoacid A to Monoacid B generally falls within the range of about 1:1 to about 4:1, depending upon the amount of the BPD mixture used.

BACKGROUND OF THE INVENTION

Photodynamic therapy (PDT) involves the action of light on a photosensitizer retained in diseased, especially cancerous tissue to produce selective cell/tissue kill. The application to the treatment of cancer and other disease states depends upon the relative selective retention of the agent in a tumor or other cancerous tissue, low systemic toxicity and the ability of the activating light to reach the diseased site. Sensitizers in clinical use include the porphyrin derivatives such as hematoporphyrin and a purified form known as dihematoporphyrin.

The sensitizers are chosen for their low systemic toxicity and are retained in most malignant tissue at levels sufficient to elicit a localized photosensitized reaction when activated by light near 630 nm (about 600 nm to about 800 nm). In many cases, the tissues surrounding or overlying the tumors have significantly lower levels of drug allowing for a relative selectivity in the destruction of the malignant tissue.

Porphyrins are naturally occuring compounds which, upon activation by light generate singlet oxygen and possibly superoxide and hydroxyl radicals. This light activation and the generation of reactive chemistry is believed to be responsible for the anti-tumor activity that many of these agents possess. Porphyrins are preferentially accumulated by tumor cells and provide the basis for PDT. This anticancer treatment involves parental, oral or topical administration of the porphyrin and, following accumulation by the tumor, its activation by a laser light directed onto the tumor via a flexible fibre optic tube (See, for example, Dougherty, T. J. In *Method in Porphyrin Photosensitization*, Edited by D. Kessel, pp. 313-328, 1985 by Plenum Press, New York). Extensive clinical studies with hematoporphyrin derivative (HpD) and Photofrin ® (a mixture of dihematoporphyrin ethers/esters) have been documented in the literature with good success (See, for example, Dougherty, T. J., *Photochem. Photobiol.*, 46, 569 (1987); Kessel, et al., *Photochem. Photobiol.*, 46 563 (1987); Dougherty, T. J., *Semin. Surg. Oncol.*, 2, 24 (1986); McCaughan, J. S., *Photochem. Phtobiol.* 46, 903 (1987); and Gomer, C. J., *Semin. Hematol.*, 26(1) 27 (1989)). This treatment however, is generally limited to light accessible carcinomas such as carcinomas of the lung, bladder, skin, etc.

Most clinical studies involving PDT have utilized hematoporphyrin derivative (HPD) which consists of a mixture of porphyrin compounds (See, Dougherty, T. J., *Photochem. Photobiol.* 46, 569 (1987). However, the therapeutic use of HPD is subject to two major limitations. First, at the wavelength of light which activates the compound, the light only poorly penetrates the tissue (See Doiron, et al., pp. 281-291 In:*Porphyrins in Tumor Phototherapy*, Edited by A. Andreoni and R. Cuulbreddu, Plenum Press, New York, 1984). This effectively limits the size of the tumors that can be treated. Second, HPD tends to accumulate in the skin of patients rendering the patients photosensitive. In most instances, patients must avoid sunlight for up to 6 weeks.

At present the most widely studied compounds for use in PDT are certain dyes, for example, porphyrins and structurally related compounds such as the chlorins, chlorophylls and purpurins, which occur naturally in animals and plants, and phthalocyananines which are synthetic molecules. A few other structurally distinct comounds have also been studied. All of the compounds which have been investigated for use in PDT have the same characteristics in common; i.e., they are pure compounds having well defined structures and absorb light in the range of 600 to 800 nm.

Benzoporphyrin derivative (BPD) represents a second generation of photosensitizers which are superior to HPD. BDP is a chlorin-like porphyrin composed of four structural analogues following synthesis. All four analogues have an identical reduced tetrapyrrol porphyrin ring. Each analogue differs only by the position of a cyclohexadiene ring which may be fused either at ring A or ring B of the porphyrin (A or B analogues) and the presence of either two acid groups (diacids) or one acid and one ester group (monoacids) at rings C and D of the porphyrin (See FIG. 1). All four analogues are hydrophobic, absorb red light at about 700 nm and efficiently produce singlet oxygen. Despite the sensitivity of all four molecules, they differ in their light activated cytoxicity in vitro and in vivo.

Two clear advantages are presented by BPD. The first is that the compound is activated by light of a longer wavelength than activates HPD. The longer wavelength light can penetrate deeper into tissue. In addition, its properties should markedly reduce patient photosensitivity.

BPD, however, suffers from the drawback that it is not water-soluble and its pharmaceutical application requires the development of a suitable delivery vehicle for parenteral administration.

Liposomes are completely closed structures comprising lipid bilayer membranes containing an encapsulated aqueous volume. Liposomes may contain many concentric lipid bilayers separated by aqueous channels (multilamellar vesicles or MLVs), or alternatively, they may comprise a single membrane bilayer (unilamellar vesicles). The lipid bilayer is composed of two lipid monolayers having a hydrophobic "tail" region and a hydrophilic "head" region. In the membrane bilayer, the hydrophobic (nonpolar) "tails" of the lipid monolayers orient toward the center of the bilayer, whereas the hydrophilic (polar) "heads" orient toward the aqueous phase. The basic structure of liposomes may be made by a variety of techniques known in the art.

Liposomes have typically been prepared using the process of Bangham et al., (1965 *J. Mol. Biol.*, 13: 238–252), whereby lipids suspended in organic solvent are evaporated under reduced pressure to a dry film in a reaction vessel. An appropriate amount of aqueous phase is then added to the vessel and the mixture agitated. The mixture is then allowed to stand, essentially undisturbed for a time sufficient for the multilamellar vesicles to form. The aqueous phase entrapped within the liposomes may contain bioactive agents, for example drugs, hormones, proteins, dyes, vitamins, or imaging agents, among others.

Liposomes may be reproducibly prepared using a number of currently available techniques. The types of liposomes which may be produced using a number of these techniques include small unilamellar vesicles (SUVs) [See Papahadjapoulous and Miller, *Biochem. Biophys. Acta.*, 135, p. 624–638 (1967)], reverse-phase evaporation vesicles (REV) [See U.S. Pat. No. 4,235,871 issued Nov. 25, 1980], stable plurilamellar vesicles (SPLV) [See U.S. Pat. No. 4,522,803, issued Jun. 11, 1985], and large unilamellar vesicles produced by an extrusion technique as described in U.S. patent application Ser. No. 310,495 filed Feb. 13, 1989, Cullis et. al., entitled "Extrusion Technique for Producing Unilamellar Vesicles", relevant portions of which are incorporated herein by reference.

Another class of multilamellar liposomes are those characterized as having substantially equal lamellar solute distribution. This class of liposomes is denominated as stable plurilamellar vesicles (SPLV) as defined in U.S. Pat. No. 4,522,803 to Lenk, et al., monophasic vesicles as described in U.S. Pat. No. 4,588,578 to Fountain, et al. and frozen and thawed multilamellar vesicles (FATMLV) wherein the vesicles are exposed to at least one freeze and thaw cycle; this procedure is described in cullis et al., U.S. patent application Ser. No. 122,613, filed Nov. 17, 1987, U.S. Pat. No. 4,975,282 issued Dec. 4, 1990 PCT Publication No. 87/00043, Jan. 15, 1987, entitled "Multilamellar Liposomes Having Improved Trapping Efficiencies". U.S. Pat. No. 4,721,612 to Janoff et al. describes steroidal liposomes for a variety of uses. The teachings of these references as to preparation and use of liposomes as well as other relevant sections are incorporated herein by reference.

OBJECTS OF THE PRESENT INVENTION

It is an object of the present invention to provide a liposomal benzoporphyrin composition.

It is an additional object of the present invention to provide a storage stable liposomal benzoporphyrin composition.

It is a further object of the present invention to provide a sized liposomal benzoporphyrin product.

It is still an additional object of the present invention to provide a liposomal benzoporphyrin composition wherein substantially all of the benzoporphyrin is inserted within the phospholipid bilayers and substantially none is found in the aqueous medium.

It is yet another object of the present invention to provide a method for making liposomal benzoporphyrin compositions.

It is still a further object of the present invention to provide a method for treating cancerous tissue using the liposomal porphyrin compositions of the present invention.

BRIEF DESCRIPTION OF THE INVENTION

The present invention relates to the discovery that benzoporphyrin derivatives (BPD), for example, diacids and monoacids and in particular, Monoacid A, which are otherwise insoluble in aqueous systems, may be incorporated into liposomes at high drug to lipid ratios. These pharmaceutical compositions of the present invention are especially useful for treating cancerous tissue by the therapeutic technique known as photodynamic therapy. These compositions are also useful as anti-viral agents.

In one aspect, the present invention also relates to a method of inserting benzoporphyrin into the bilayer of liposomes of the present invention using a co-lyophilization process. In this method, the resulting liposomes contain large amounts of benzoporphyrin within the liposome bilayer and a substantial absence of benzoporphyrin in the encapsulated buffer. The present invention is thus amenable to the low-cost manufacture of benzoporphyrin liposomal compositions.

Drug to lipid ratios of up to 209 $\mu g/\mu$mole of lipid are possible using BPD-Monoacid A in Egg Phosphatidyl Choline (EPC). Thus, in a preferred embodiment of the present invention benzoporphyrin containing pharmaceutical compositions comprising substantially all Monoacid A in liposomes are presented. In addition, in liposomal preparations prepared from mixtures of BPD-Monoacid A and BPD-Monoacid B, for example about 1:1 (w/w), BPD-Monoacid A may be incorporated within the liposomes to a much larger extent (generally, within a range of about 1:1 to about 4:1 by weight) than is BPD-Monoacid B, depending upon the amount of BPD encapsulated.

The liposomes of the present invention are amenable to sizing by methods readily available in the art. Sized liposomes of the present invention show no tendency to aggregate. These sized liposomes efficiently maximize drug efficacy and in addition, have been shown to allow sterilization of the formulation by terminal filtration, a clear manufacturing advantage.

The benzoporphyrin derivatives, including the diacids and monoacids, have been shown to insert themselves into the lipid bilayer of the liposomes with substantially no benzoporphyrin to be found in the aqueous medium. This is a surprising result. In the present invention, we have determined the maximum level of incorporation of BPD-MA and BPD-MB as a function of the liposome composition. Surprisingly, high drug to lipid ratios can be achieved, particularly for BPD-MA. This information allows us to prepare liposomal benzoporphyrin mixtures where substantially all of the drug is intercalated into the lipid bilayer and substantially none is found in the aqueous medium. This not only maximizes the yield of liposomal benzoporphyrin but also greatly simplifies manufacturing because additional steps to remove drug unassociated with the liposomes are not required.

Certain benzoporphyrin-containing liposomes have been shown to be storage stable after lyophilization in the presence of protective sugars, for example as disclosed by Janoff, et al., in U.S. Pat. No. 4,880,635, issued Nov. 14, 1989, PCT Application Number PCT/US85/01502, International Publication Number WO 86/01103, published Feb. 27, 1986, relevant portions of which are incorporated by reference herein.

In another aspect of the present invention, a therapeutic method for treating cancerous cells and tissues with benzoporphyrin containing liposomes of the present invention is presented. In this method, a patient is treated with an effective amount of benzoporphyrin containing liposomes and the cancerous tissue containing the benzoporphyrin which results from this treatment is then exposed to a light source of wavelength ranging from about 600 to about 850 nm, preferably a wavelength within the red visible spectrum (approximately 700 nm) for a time sufficient to produce adequate cell kill.

DETAILED DESCRIPTION OF THE INVENTION

Figure 1:
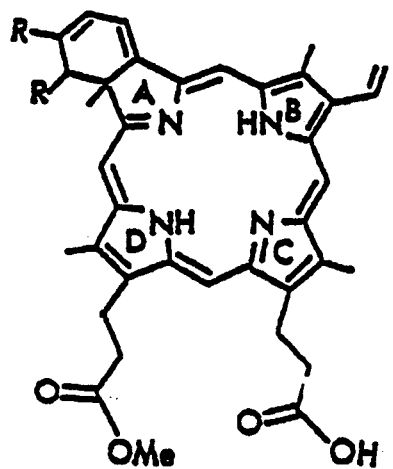
FIG. 1 presents the structures of benzoporphyrin derivatives (BPD) as the diacids or the Monoacids. Four structures are presented: Monoacid A, Monoacid B (structures 1 and 2 of FIG. 1, and Diacid A and Diacid B (structures 3 and 4 of FIG. 1), depending upon the pyrrole ring to which the cyclohexadiene moiety is fused.
Figure 1:
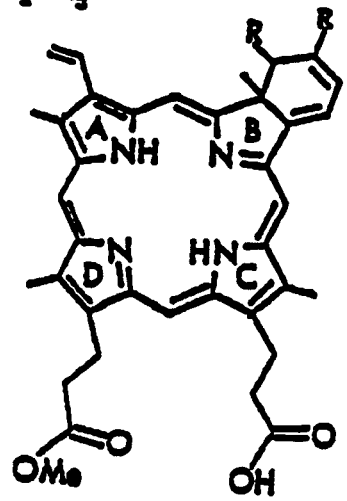
Figure 1:
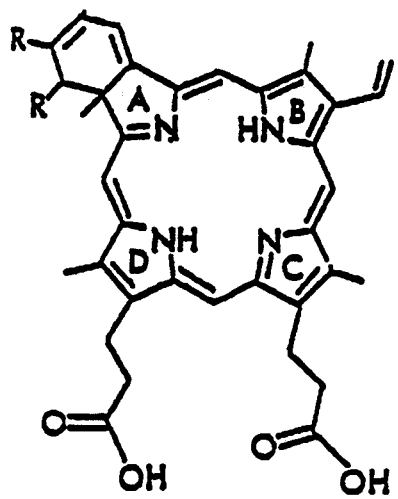
Figure 1:
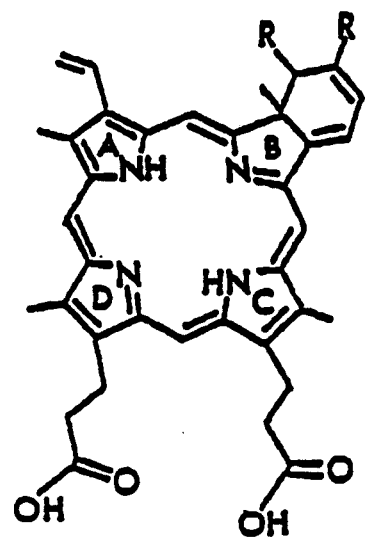

The present invention relates to pharmaceutical compositions comprising a cancer treating effective amount of a benzoporphyrin derivative in liposomes. In particular, the present invention relates to the discovery that the bulky benzoporphyrin (BPD) analogues, especially including BPD Monoacid A (BPD-MA) and BPD Monoacid B (BPD-MB) as set forth in FIG. 1 are readily inserted into the bilayer of liposomes. In the BPD containing liposomes of the present invention, it has surprisingly been discovered that BPD-MA may be inserted into the bilayers of liposomes in a much greater concentration than can the BPD-MB analogues.

Benzoporphyrin derivative (BPD) is a chlorin-like photosensitizer and is represented by four analogues, two of which are diacids and two of which are monoacids. All four analogues have an identical reduced tetrapyrrol porphyrin ring. Each analogue differs only by the position of a cyclohexadiene ring which may be fused either at ring A or ring B of the porphyrin (ring A or B analogues) and the presence of either one or two acid groups (monoacids and diacids, respectively) at rings C and D of the porphyrin moiety (See FIG. 1). All four analogues are hydrophobic, absorb red light at about 700 nm and efficiently produce singlet oxygen. Despite the sensitivity of all four molecules, they differ in their light activated cytoxicity in vitro and in vivo.

Recent studies have shown that the freely administered monoacids show much greater cytotoxicity and potential use as chemotherapeutic agents in vitro than do the diacids. In a preferred embodiment of the present invention, liposomes containing BPD-MA and mixtures of BPD-MA and BPD-MB inserted substantially exclusively within the bilayer of the liposomes are presented. In a preferred embodiment of the present invention, BPD containing liposomes are prepared from a mixture containing about a 1:1 (w/w) ratio of BPD-MA and BPD-MB. The amount of BPD-MB inserted within the liposomes does not exceed about 50 $\mu$g BPD-MB/$\mu$mole of phospholipid. When liposomes are made from a 1:1 (w/w) mixture of BPD-MA and BPD-MB, the amount of BPD-MA inserted within the bilayer of the liposomes represents approximately about 50% to about 80% by weight of the total amount of BPD. In other preferred embodiments of the present invention liposomal compositions are described containing extremely high drug to lipid ratios comprising substantially exclusively BPD-MA inserted into the bilayers of liposomes. The insertion of BPD almost exclusively into the bilayers of liposomes and the high drug to lipid ratios that are obtainable are unexpected results.

The present invention also relates to BPD-containing liposomes which are sized after formation. In this aspect of the present invention, BPD-containing liposomes are sized by any method readily available in the art, including extrusion. Any extrusion process available in the art may be used to produce the sized liposomes of the present invention and the extrusion of the liposomes of the present invention may be performed either through a series of filters of sequentially smaller pore size or directly through 100 nm pore size filters under high pressure. Particularly preferred extrusion processes for use in the present invention include those disclosed in Cullis, et al., U.S. patent application Ser. No. 310,495, filed Feb. 13, 1989, pending PCT Application PCT/US85/01161, Publication Number WO 86/00238 entitled "Extrusion Techniques for Producing Unilamellar Liposomes" published Jan. 16, 1986, relevant portions of which are incorporated by reference herein.

In the extrusion aspect of the present invention, BPD containing liposomes are passed through filters having pore sizes generally about 100 nm to produce sized liposomes ranging from about 100 to about 120 nm in diameter. The sized liposomes of the present invention are associated with maximimal drug efficacy. The filters used for sizing are generally made of polycarbonate, but the filters may be made of any durable material which does not interact with the liposome and which is sufficiently strong to allow extrusion under sufficient pressure. Preferred filters include "straight through" filters because they generally can withstand the higher pressure of the preferred extrusion processes of the present invention. Although less preferred, "tortuous path" filters may also be used.

In certain embodiments, the liposomes used to form the present invention are themselves formed using the LUVET apparatus described in copending U.S. patent application entitled "Extrusion Technique for Producing Unilamellar Vesicles" Ser. No. 310,495, filed Feb. 13, 1989, pending relevant portions of which are incorporated herein by reference.

Liposomes of the present invention are preferably formed by a method in which the BPD is substantially exclusively, i.e., completely or almost completely, inserted into the liposomal bilayer. Insertion of BPD into the lipid bilayer is generally achieved by a co-lyophilization of the BPD:lipid mixture from a solvent or solvent mixture, for example, benzene:methanol following by hydration in aqueous media. The process is not restricted, however, to the specific system described; any solvent (or solvent mixture) in which both components are soluble could serve as the starting point. Thus, for example, a combination of non-polar solvents or alternatively a polar and non-polar mixture of solvents could be used. The solvent could then be removed by lyophilization, rotary evaporation or under reduced pressure in the presence of an aqueous emulsion (See, for example the SPLV procedure of Gruner, et al., *Biochemistry*, 24, 2833 (1985). In addition to the above preferred method, it is possible to admix the BPD in a water-miscible solvent with an aqueous dispersion of vesicles to achieve membrane insertion. Other methods readily available in the art may also be used to produce the liposomes of the present invention.

In certain cases, especially when BPD-Diacids are being inserted into liposomes, the liposomes according to the present invention may be formed with a transmembrane potential i.e., a proton (H+) gradient across the bilayers, see, for example, copending U.S. patent application Ser. No. 284,751, Bally et. al., entitled "Encapsulation of Antineoplastic Agents in Liposomes", filed Dec. 12, 1988, U.S. Pat. No. 4,901,962 relevant portions of which are incorporated herein by reference; this potential difference may be effected by the ionic concentrations of the internal versus the external media of the liposome.

The present invention also relates to storage stable BPD containing liposomes. For example, after loading the liposomes with BDP, the liposomes may then be dehydrated either in the presence or absence of sugars such as trehalose, and may be stored in this state for indefinite periods of time; see U.S. Pat. No. 4,880,635, Janoff et. al., entitled "Dehydrated Liposomes," issued Nov. 14, 1989, relevant portions of which are incorporated herein by reference. To maximize lipid and drug stability, storage of the preparation in a dehydrated form or at −20° C. would be desirable.

The liposomes used in the present invention can have a variety of compositions and internal contents, and can be in the form of multilamellar, unilamellar, or other types of liposomes, or more generally, lipid-containing particles, now known or later developed. For example, the lipid-containing particles can be in the form of steroidal liposomes, stable plurilamellar liposomes (SPLVs), monophasic vesicles (MPVs), or lipid matrix carriers (LMC) of the types disclosed in commonly assigned U.S. Pat. Nos. 4,721,630, issued Jan. 26, 1988, 4,522,803, issued Jun. 11, 1985 and 4,588,578, issued May 13, 1986 respectively, the pertinent portions of which are incorporated herein by reference.

The liposomes of the present invention may be formed from a number of lipids. Lipids which can be used in the liposome formulations of the present invention include synthetic or natural phospholipids and may include phosphatidylcholine (PC), phosphatidylethanolamine (PE), phosphatidylserine (PS), phosphatidylglycerol (PG), phosphatidic acid (PA), phosphatidylinositol(PI), sphingomyelin (SPM) and cardiolipin, among others, either alone or in combination. The phospholipids useful in the present invention may also include dimyristoylphosphatidylcholine (DMPC) and dimyristoylphosphatidylglycerol (DMPG). In other embodiments, distearylphosphatidylcholine (DSPC), dipalmitoylphosphatidylcholine (DPPC), or hydrogenated soy phosphatidylcholine (HSPC) may also be used. Dimyristoylphosphatidylcholine (DMPC) and diarachidonoylphosphatidylcholine (DAPC) may similarly be used. Due to the elevated transition temperatures ($T_c$) of lipids such as DSPC ($T_c$ of about 54° C.), DPPC ($T_c$ of about 41° C.) and DAPC ($T_c$ of about 66° C.), such lipids are preferably heated to slightly above their $T_c$, e.g., up to about 5° C. higher than the $T_c$, in order to make these liposomes. Preferred liposomes of the present invention comprise egg phosphatidyl choline (EPC) and dimyristroyl phosphatidyl choline (DMPC). In especially preferred embodiments, especially those in which very high drug to lipid ratios are produced, egg phosphatidylcholine is used.

In a number of embodiments of the present invention, a steroidal component may be added to the liposome. For purposes of the present invention any component including the above-described phospholipids which may be used to produce a liposome either alone or in combination with a phospholipid is termed a liposome producing lipid. In certain embodiments of the present invention, the amount of liposome forming lipid may range from about 10% to about 100% by weight of the liposome and in preferred embodiments of the present invention, the liposome producing lipid comprises at least about 50 mole percent of the total weight of the lipids of the liposome. Any of the above-mentioned phospholipids may be used in combination with at least one additional component selected from the group consisting of cholesterol, cholestanol, coprostanol or cholestane. In addition, polyethylene glycol derivatives of cholesterol (PEG-cholesterols), as well as organic acid derivatives of sterols, for example cholesterol hemisuccinate (CHS) may also be used alone or preferably in combination with any of the above-mentioned phospholipids. Organic acid derivatives of alphatocopherol hemisuccinate, (THS) may also be used. CHS- and THS-containing liposomes and their tris salt forms may generally be prepared by any method known in the art for preparing liposomes containing sterols, so long as the resultant phospholipid-sterol mixture yields stable liposomes. In particular, see the procedures of Janoff, et al., U.S. Pat. No. 4,721,612, issued Jan. 26, 1988, entitled "Steroidal Liposomes" and Janoff, et al., U.S. Pat. No. 4,861,580, issued Aug. 29, 1989, PCT Publication No. 87/02219, published Apr. 23, 1987, entitled "Alpha Tocopherol-Based Vehicles", relevant portions of which are incoporated by reference herein. In certain embodiments containing cholesterol, the cholesterol is utilized in combination with EPC in a molar ratio of cholesterol to EPC of about 45:55.

Another aspect of the present invention relates to storage stable BPD-containing liposomes. Either before or after extrusion but preferably after extrusion to produce sized liposomes, the liposomes loaded with benzoporphyrin may be dehydrated for storage.

The BPD-containing liposomes of the present invention may be dehydrated using standard freeze-drying equipment or equivalent apparatus, and, if desired, the liposomes and their surrounding medium can be frozen in liquid nitrogen before being dehydrated. Alternatively, the liposomes can also be dehydrated without prior freezing, by simply being placed under reduced pressure. Dehydration generally requires the presence of one or more protective sugars in the preparation. A variety of sugars can be used, including such sugars as, for example, trehalose, maltose, sucrose, glucose, lactose, and dextran. In general, disaccharide sugars have been found to work better than monsaccharide sugars, with the disaccharide sugars trehalose and sucrose being most effective.

The one or more sugars are included as part of either the internal or external media of the BPD-containing liposomes. Most preferably, the sugars are included in both the internal and external media so that they can interact with both the inside and outside surfaces of the liposomes' membranes. Inclusion in the internal medium is accomplished by adding the sugar or sugars to the solute which the liposomes are to encapsulate. Since in most cases this solute also forms the bathing medium for the finished liposomes, inclusion of the sugars in the solute also makes them part of the external medium. Of course, if an external medium other than the original solute is used, e.g., to create a transmembrane potential for loading the BPD, the new external medium should also include one or more of the protective sugars.

In the case of dehydration without prior freezing, if the liposomes being dehydrated have multiple lipid layers and if the dehydration is carried out to an end point where there is sufficient water left in the preparation so that a substantial portion of the membranes retain their integrity upon rehydration, the use of one or more protective sugars may be omitted. It has been found preferable if the preparation contains at the end of the dehydration process at least about 2%, and most preferably between about 2% and about 5%, of the original water present in the preparation prior to dehydration.

Once the liposomes have been dehydrated, they can be stored for extended periods of time until they are to be used. When the dehydrated liposomes are to be used, rehydration is accomplished by simply adding an aqueous solution, e.g., distilled water, to the liposomes and allowing them to rehydrate.

In making storage stable BPD-containing liposomes, the liposomes can be loaded with BPD, for example, using conventional techniques, dehydrated for purposes of storage, shipping, and the like, and then rehydrated at the time of use.

When the dehydrated liposomes are to be used, rehydration is accomplished by simply adding an aqueous solution, e.g., distilled water or an appropriate buffer, to the liposomes and allowing them to rehydrate. The liposomes may be resuspended into the aqueous solution by gentle swirling of the solution. The rehydration can be performed at room temperature or at other temperatures appropriate to the composition of the liposomes and their contents.

BPD-containing liposomes of the present invention may be administered to a subject such as a mammal, including humans for the treatment of neoplasia. For administration to humans in the treatment of neoplasia, the prescribing physician will ultimately determine the appropriate dose for a given human subject, and this can be expected to vary according to the age, weight, and response of the individual as well as the nature and severity of the patient's disease.

The mode of administration may determine the sites in the organism to which the compound will be delivered. For instance, delivery to a specific site of activity may be most easily accomplished by topical application (for example, if the treatment is to be directed onto the skin for treatment of skin cancer). Such topical application may be in the form of creams or ointments.

The liposomes of the present invention may be administered to a subject, for example a mammal including humans. The composition may be delivered to such a subject parenterally in a pharmaceutically acceptable carrier or diluent such as phosphate buffered saline. When used parenterally, the amount of liposomes used will be determined by the physician, and the treatment procedure as determined by the size of the tumor or other condition.

The BPD containing liposomes may be administered alone but will generally be administered in admixture with a pharmaceutical carrier selected with regard to the intended route of administration and standard pharmaceutical practice. The BPD containing liposomes of the present invention may be injected parenterally, for example, intravenously, intramuscularly, or subcutaneously. For parenteral administration, the liposomes may best be used in the form of a sterile aqueous solution which may contain other solutes, for example, sufficient salts, glucose or dextrose to make the solution isotonic.

In certain cases, an oral mode of administration may be contemplated, in which case the BPD containing liposomes of the present invention can be used in the form of tablets, capsules, lozenges, troches, powders, syrups, elixirs, aqueous solutions and suspension, and the like. In the case of tablets, carriers which can be used include lactose, sodium citrate, and salts of phosphoric acid. Various disintegrants such as starch, and lubricating agents, for example, stearic acid may be used. For oral administration in capsule form, useful diluents are lactose and high molecular weight polyethylene glycols. When aqueous suspensions are required for oral use, certain sweetening and/or flavoring agents can be added.

Benzoporphyrin derivatives, including their pharmaceutically acceptable salts and equivalents, are contemplated for use in the present invention. Determination of compatibilities of the above listed agents with and the amounts to be utilized in compositions of the present invention are within the ordinary skill in the formulation art. The stability and applicability of individual pharmaceutical agents are well within the ordinary skill of the practitioner in this art.

It will be appreciated that the actual preferred amounts of BPD utilized in a specific case may vary according to the severity of a disease condition and the expected pharmacokinetics of BPD in the individual patient. Dosages for a given host can be determined using conventional considerations, e.g., by customary comparison of the differential activities of the subject bioactive agent by means of an appropriate, conventional pharmacological protocol.

In the therapeutic aspect of the present invention, a mammal, including humans, with a neoplasia or related cancerous tissue such as a tumor, will be treated by administering an effective amount of BPD containing liposomes by an oral, topical or parenteral route. After a period of time sufficient to allow sufficient delivery of BPD to the diseased site, the site is then treated with a light source, preferably a laser light source of high intensity at a wavelength of light which will activate the BPD to produce cytotoxicity, generally within the range of about 600 to about 800 nm. A preferred wavelength of light ranges in the visible red range, i.e., from about 700–725 nm.

The following examples are provided for purposes of illustration only and are not to be viewed as a limitation of the scope of the invention.

EXAMPLES

MATERIALS AND METHODS

Benzoporphyrin as the monoacid A, monoacid B or a 1:1 mixture of the two was synthesized by the method as described in Richter, et al., *Jour. Nat. Can. Inst.*, 79, 1327 (1987) and Pangka, et al., *J. Org. Chem.*, 51, 1094 (1986). Briefly, protoporphyrin prepared from hematoporphyrin as described in detail by Dinello and Chang, pp. 290–294 of *The Porphyrins*, Vol 1, Dolphin, D., Ed., 1978 by Academic Press, New York, N.Y. is reacted with dimethyl acetylenedicarboxylate to give intermediate Diels-Alder adducts, which are subsequently rearranged with 1,5-diazabicyclo[5.4.0]undec-5-ene. The resulting diastereomeric mixture of methyl esters is then hydrolyzed with 25% aqueous hydrochloric acid at room temperature for 5 hours in the dark. The resulting product is then frozen in liquid nitrogen, and dried under high vacuum. The crude, isolated BPD (predominantly a 1:1 mixture of the monoacid analogues and a minor component of a mixture of the diacid analogues) may be used without further purification. The crude mixture of BPD may be further purified to its pure Monoacid form (both monoacid A and B being present in a 1:1 ratio), its Monoacid A isomer (cyclohexadiene ring fused at ring A as in structure A of FIG. 1) or its Monoacid B isomer (cyclohexadiene ring fused at ring B as in structure B of FIG. 1) by reverse phase preparative HPLC (Solvent system A=$H_2O$/$CH_3CN$/$CH_3COOH$, 10/10/0.5 and B=$H_2O$/THF/$CH_3COOH$, 10/10/0.5; Initial 60% A:40% B for 5 minutes followed by gradient of 40% B to 70% B over 20 minutes. Ultrasphere 5 $\mu$m ODS, 4.6 mm packing in column), Richter, et al., *J. Nat. Can. Inst.*, 79, 1327 (1987). BPD-MA will come off the column first, followed by BPD-MB. The physical properties of these analogues do not differ significantly nor do they differ in their ability to produce singlet oxygen. The Monoacid A and Monoacid B analogues are significantly more active than are the Diacid A and B analogues.

Dimyristoylphosphatidylcholine (DMPC) and egg phosphatidylcholine (EPC) were obtained from Avanti Polar Lipids (USA). Cholesterol (standard for chromatography) was purchased from Sigma (Canada). All salts and organic solvents were of analytical grade. $^3$H-dipalmitoylphosphatidylcholine (DPPC) was supplied by New England Nuclear.

Phospholipids were quantified either by phosphate analysis (See, for example, Chen, et al., *Anal. Chem.*, 28, 1756 (1956) following perchloric acid digestion or by liquid scintillation counting of samples containing $^3$H-DPPC. Benzoporphyrin was quantified from its absorbance at 686 nm in ethanol:water (80:20 v/v) employing a Shimadzu UV-265 spectrophotometer.

EXAMPLE 1

Preparation of Lyophilized Benzoporphyrin:lipid Vesicles

Vesicles of EPC, EPC/Chol or DMPC containing benzoporphyrin (BPD-MA, BPD-MB and BPD-MA/BPD-MB 1:1 ) were prepared in 250 mM lactose, 50 mM mannitol, 100 mM NaCl, 20 mM citrate at pH 6.0. Aliquots (1 ml) in 10 ml glass vials were placed in a FTS Dura-Stop tray dryer pre-cooled to $-35°$ C. When the sample temperature reached $-34°$ C. the vaccum was switched on and the sample temperature was allowed to fall to $-40°$ C. The shelf temperature was then maintained at $-35°$ C. for 16 hours at a vacuum of <20 microns Hg. The shelf temperature was then raised as follows: $-25°$ C. for 8 hours, $-15°$ C. for 16 hours, $-5°$ C. for 1 hour, $+5°$ C. for 1 hour, $+15°$ C. for 1 hour and $+30°$ C. for 1 hour. Samples were then stoppered under full vacuum, removed and stored in the dark at $-70°$ C. This process yielded a homogeneous dark green lyophilate which was used to prepare liposomal benzoporphyrin of the present invention.

EXAMPLE 2

Preparation of Liposomal Benzoporphyrin

A lyophilized lipid:benzoporphyrin mixture (BPD-MA/BPD/MB 1:1, other BPD analogues can be used) obtained from benzene: methanol (95:5 v/v) was hydrated in 150 mM NaCl, 20 mM Hepes pH 7.4 (unless otherwise stated) and dispersed by gentle vortexing. Dispersions containing DMPC were maintained at 30° C. (above the gel to liquid-crystalline phase transition temperature) to produce multilamellar vesicles. These MLVs were then sized by extrusion through two stacked 100 nm Nucleopore polycarbonate filters as described by Hope, et al., *Biochim. Biophys. Acta*, 812, 55 (1985) employing an Extruder (Lipex Biomembranes). EPC and EPC:Chol samples were sized at room temperature (25° C.) and DMPC containing liposomes were extruded at 30° C.

The size distributions of the liposomes containing BPD were determined using quasi-electric light scattering. The sample was diluted 1:50 into filtered 150 mM NaCl, and then analyzed at 23° C. using a Nicomp 370 submicron particle size operating at 632.8 nm and 5 mW.

Figure 2:
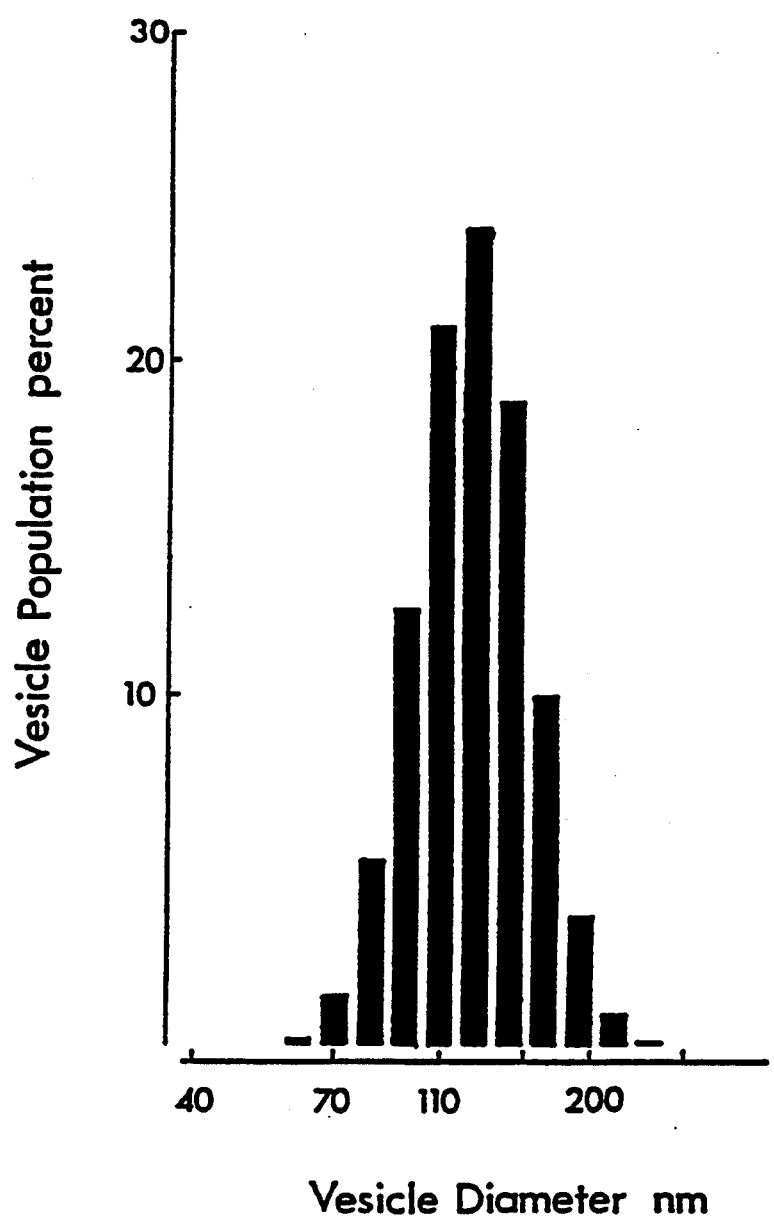
FIG. 2 shows the Gaussian size distribution analysis of egg phosphatidylcholine vesicles containing benzoporphyrin obtained by quasielectric light scattering.

When benzoporphyrin co-lyophilized with EPC was hydrated in aqueous buffer a dark green suspension of MLVs was formed. This material can be converted to large unilamellar vesicles by extrusion through 100 nm polycarbonate filters. Ratio of BPD to phospholipid did not exceed the maximum ratio the bilayers can accommodate (see for example the results for incorporation of BPD-MA in Table 1, below). No residue was observed on the filters following extrusion. The resultant vesicles have a mean diameter of about 120 nm (See FIG. 2) and show no tendency to aggregate. No precipitation of benzoporphyrin was observed on storage of the vesicles for several weeks in the dark at 4° C.

EXAMPLE 3

Preparation of DMPC Benzoporphyrin Monoacid A

Dimyristoyl phosphatidylcholine (DMPC) and benzoporphyrin monoacid A (BPD-MA) are co-lyophilized from benzene:methanol (95:5) at a ratio of 100 $\mu$g BPD-MA/umole DMPC. The dry powder is hydrated in 500 mM lactose, 100 mM mannitol, 100 mM NaCl, 20 mM citrate pH 6.0 at a BPD-MA concentration of 10 mg/ml (100 μmole DMPC/ml) at 30° C. for 30 minutes with gentle vortexing. The large multilamellar vesicles thus formed are sized to about 110–120 nm by extrusion through 2 stacked 0.1 micron Nucleopore polycarbonate filters at 30° C. The BPD-MA liposomal suspension is then lyophilized by placing 1 ml aliquots in 10 ml glass vials which are then placed in a tray dryer precooled to −35° C. When the sample temperature reaches −34° C. the vacuum is switched on and the sample temperature allowed to fall to −40° C. The shelf temperature is maintained at −35° C. for 16 hours at a vacuum of <20 microns Hg. The shelf temperature is then raised as follows: −25° C. for 8 hours, −15° C. for 16 hours, −5° C. for 1 hour, +5° C. for 1 hour, +15° C. 1 hour and +30° C. for 1 hour. Samples are then stoppered under full vacuum, removed and stored in the dark at −20° C.

Prior to administration, the lyophilized liposomal benzoporphyrin is rehydrated with sterile water for injection at 30° C.

EXAMPLE 4

Confirmation of BPD Intercalation in Liposomes

Figure 3:
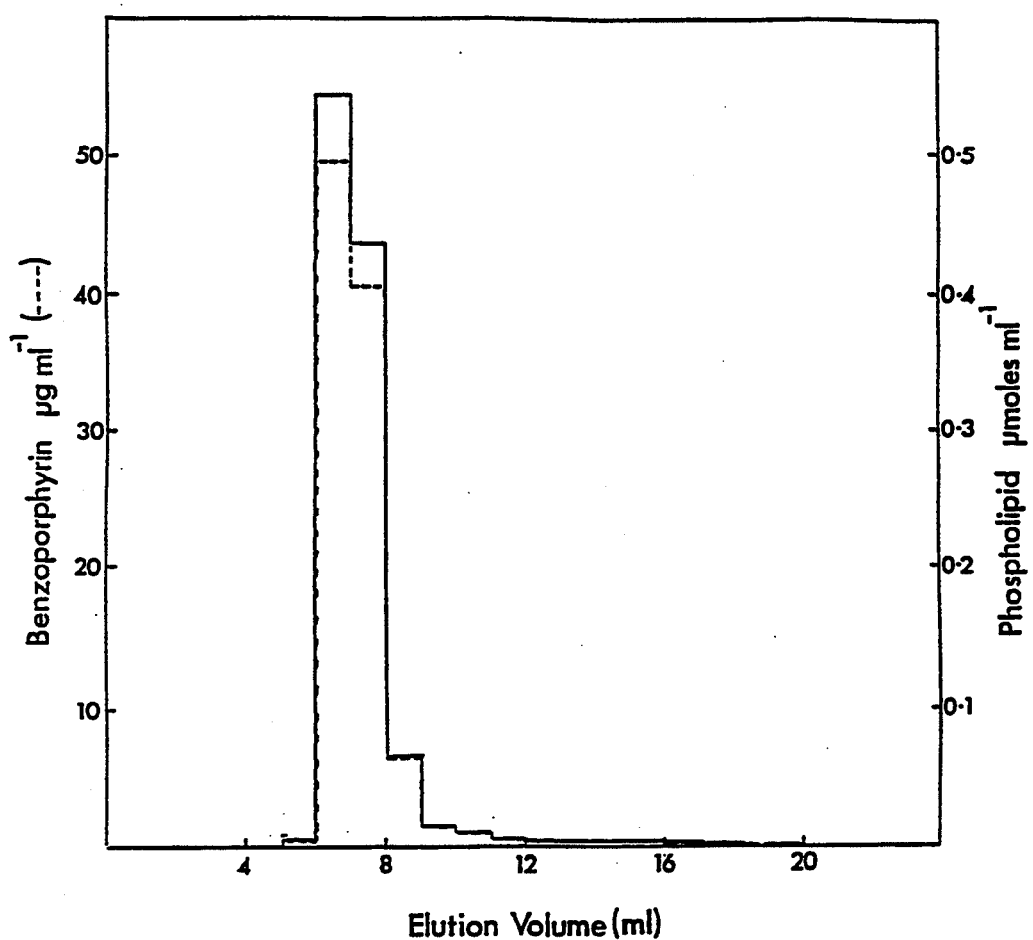
FIG. 3 shows the elution profile of egg phosphatidylcholine-benzoporphyrin vesicles on a Sephadex G-50 gel exclusion column. The vesicles contained 110 $\mu$g BPD/umol EPC.

To determine that all of the BPD was inserted within the lipid bilayer and no free drug is present within the aqueous medium, the sample was eluted on a Sephadex G-50 (fine) gel exclusion column. The elution profile is shown in FIG. 3 and indicates that the BPD and lipid co-elute with no evidence for non-vesicle associated drug. The BPD:lipid ratio is constant over the elution profile and identical to the starting material. This is true for compositions containing Monoacid A, Monoacid B, or mixtures, thereof, provided that the initial BPD lipid mixture did not exceed the level of drug that the liposomes can accommodate (see Table 1, below). In control experiments where an equivalent amount of BPD in aqueous buffer was added to the column, all of the drug remained as an insoluble layer on top of the Sephadex G-50.

EXAMPLE 5

Determination of Maximum Level of BPD Incorporation (Monoacid A)

To determine the maximum level of incorporation of BPD-MA into liposomes, lyophilized mixtures of drug and either EPC or EPC:Chol were prepared with varying initial drug:lipid ratios. Following sample hydration the mixtures were sized by extrusion through 100 nm filters. In samples where the initial ratio of drug-to-lipid was greater than the solubility of the BPD in the vesicle membrane (see Table 1, below), the excess BPD precipiated out of solution and was retained on the polycarbonate filters. The BPD:lipid ratio was then determined in the extruded vesicles. As evidenced in Table 1, EPC vesicles can retain about 209 μg BPD Monoacid A/μ-mole phospholipid. When cholesterol is present in the bilayer, the maximum level of BPD Monoacid A incorporation is reduced to about 120 μg/umole phospholipid (Table 1).

TABLE 1

Influence of Lipid Composition on Insertion of BPD-MA

| Lipid | Initial Benzoporrhyrin/lipid Ratio (ug Benzoporphyrin/umole lipid) | Final Ratio (ug/umole) |
|---|---|---|
| EPC | 104 | 110 |

TABLE 1-continued

Influence of Lipid Composition on Insertion of BPD-MA

| Lipid | Initial Benzoporrhyrin/lipid Ratio (ug Benzoporphyrin/umole lipid) | Final Ratio (ug/umole) |
|---|---|---|
| EPC | 156 | 170 |
| EPC | 312 | 209 |
| EPC:CHOL | 110 | 102 |
| EPC:CHOL | 147 | 113 |
| EPC:CHOL | 220 | 126 |

In addition to EPC and EPC:chol BPD Monoacid A was also incorporated into lipid vesicles comprising DMPC. This saturated phospholipid undergoes a liquid-crystalline phase transition at 23° C. The lipid:BPD mixture was hydrated and extruded at 30° C. Vesicles of DMPC:BPD were prepared at 2 mg/ml BPD (20 mg/ml DMPC) and 10 mg/ml BPD (100 mg/ml DMPC) as shown in Table 2, below. Stable association of the drug within the lipid bilayer was observed with no BPD precipitation even when the lipid mixture was stored at 4° C., i.e., below the phase transition temperature for pure DMPC. The mean diameters of DMPC:BPD vesicles prepared using 100 nm polycarbonate filters are also shown in Table 2 for both drug:lipid concentrations.

TABLE 2

Incorporation of Benzoporphyrin into DMPC Vesicles

| BPD Concentration* | Vesicle Mean Diameter | Standard Deviation |
|---|---|---|
| 2 mg/ml | 117 nm | 20.1% |
| 10 mg/ml | 114 nm | 24.3% |

*The weight ratio of phospholipid to BPD was about 10:1 for both samples.

When EPC or DMPC vesicles containing BPD in aqueous suspension were lyophilized in the presence of lactose and mannitol a homogeneous green powder was obtained. Upon injection of sterile water the powder was readily hydrated yielding a green solution visually indistinguishable from the original suspension before drying. The samples analyzed before and after lyophilization and rehydration are presented in Table 3. Little change in mean vesicle diameter was observed.

TABLE 3

Influence of Lyophilization on Size Distribution of DMPC Vesicles containing Benzoporphyrin

| Sample | Conditions | Mean Vesicle Diameter | Standard Deviation |
|---|---|---|---|
| DMPC:BPD* | Control | 109 nm | 24.1% |
| DMPC:BPD | Lyophilized | 108 nm | 33.2% |

*Control Vesicles were maintained at 4° C.

EXAMPLE 6

Monoacid B Liposomes

A comparison of the Monoacid B liposomes produced by the same method as set forth for in examples 1–3 indicated that the Monoacid B was not nearly as efficient as the Monoacid A intercalating into vesicles comprising EPC and DMPC. The Monoacid B compound co-lyophilized with either EPC or DMPC was very difficult to hydrate and extrude. Following extrusion a green residue was observed on the polycarbonate filters and the final Monoacid B ratio (55 μg/umole lipid) was less than 50% of the starting material. Thus, the maximum level of incorporation of Monoacid B into liposomes is considerably lower than for the Monoacid A (See Table 1, above).

EXAMPLE 7

Monoacid A/B Liposomes

A comparison of the liposomes containing a 1:1 mixture of Monoacid A/B produced by the same method as set forth for examples 1—3 indicated that the Monoacid A/B was not nearly as efficient as the Monoacid A intercalating into vesicles comprising EPC and DMPC, but was more efficient than was Monoacid B. Following extrusion the maximal Monoacid A/B to phospholipid ratio (110 µg/umole lipid) was somewhat less than for Monoacid A. Thus, the maximum level of incorporation of a 1:1 mixture of Monoacid A/B into liposomes is considerably lower than for the Monoacid A alone (See Table 1, above).

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the inventions those of skill in the art will readily understand. Accordingly, such variations and modifications are considered to be within the purview and scope of the invention and the following claims.

I claim:

1. A composition for treating cancerous tissue with photodynamic therapy consisting of a photosensitizing effective mount of a benzoporphyrin, which is not complexed to a metal, in liposomes, and a pharmaceutical carrier, wherein said benzoporphyrin is selected from the group consisting of benzoporphyrin monoacid A, monoacid B, diacid A, diacid B and mixtures thereof, and wherein said composition has a benzoporphyrin to lipid ratio greater than 100 µg benzoporphyrin per mole lipid.

2. The composition according to claim 1 wherein the benzoporphyrin is benzoporphyrin monoacid A.

3. The composition according to claim 1 wherein the components of said liposome comprise egg phosphatidyl choline or dimyristoylphosphatidyl choline.

4. The composition according to claim 1 wherein said liposomes are sized.

5. The composition according to claim 4 wherein said liposomes are no greater than about 120 nm in diameter.

6. The composition according to claim 1 wherein said benzoporphyrin is inserted substantially within bilayers of said liposomes.

7. The composition according to claim 1 wherein said liposomes are storage stable.

8. The composition according to claim 1 adapted for topical administration.

9. The composition according to claim 1 adapted for parenteral administration.

10. The composition according to claim 6 having a weight ratio of benzoporphyrin monoacid A to benzoporphyrin monoacid B of about 1:1 to about 4:1.

11. The composition according to claim 10 wherein the weight ratio is about 1:1.

12. The composition according to claim 2 wherein the components of the liposome comprise egg phosphatidyl choline.

13. The composition according to claim 1 wherein the benzoporphyrin is a mixture of benzoporphyrin monoacid A and monoacid B.

14. A method for treating cancerous tissue using photodynamic therapy in a patient comprising administering to said patient a composition consisting of a photosensitizing effective amount of a benzoporphyrin, which is not complexed to a metal, in liposomes, and a pharmaceutical carrier, wherein said benzoporphyrin is selected from the group consisting of benzoporphyrin monoacid A, monoacid B, diacid A,-diacid B and mixtures thereof, and wherein said composition has a benzoporphyrin to lipid ratio greater than 100 µg benzoporphyrin per mole lipid.

15. The method according to claim 14 wherein the benzoporphyrin is benzoporphyrin monoacid A.

16. The method according to claim 14 wherein the benzoporphyrin is a mixture of benzoporphyrin monoacid A and monoacid B.

17. The method according to claim 14 wherein the components of said liposome comprise egg phosphatidyl choline or dimyristoylphosphatidyl choline.

18. The method according to claim 14 wherein said liposomes are sized.

19. The method according to claim 18 wherein said liposomes are no greater than about 120 nm in diameter.

20. The method according to claim 14 wherein said benzoporphyrin is inserted substantially within bilayers of said liposomes.

21. The method according to claim 14 wherein said liposomes are storage stable.

22. The method according to claim 14 adapted for topical administration.

23. The method according to claim 14 adapted for parenteral administration.

24. The method according to claim 16 wherein the composition has a weight ratio of benzoporphyrin monoacid A to benzoporphyrin monoacid B of about 1:1 to about 4:1.

25. The method according to claim 24 wherein the weight ratio is about 1:1.

* * * * *